United States Patent
Kiremitci

(10) Patent No.: US 9,409,035 B2
(45) Date of Patent: Aug. 9, 2016

(54) OSCILLATING PHOTO LIGHT THERAPY DEVICE

(71) Applicant: Kirkor Kiremitci, Laval (CA)

(72) Inventor: Kirkor Kiremitci, Laval (CA)

(*) Notice: Subject to any disclaimer, the term of this patent is extended or adjusted under 35 U.S.C. 154(b) by 0 days.

(21) Appl. No.: 14/267,525

(22) Filed: May 1, 2014

(65) Prior Publication Data

US 2014/0350644 A1 Nov. 27, 2014

Related U.S. Application Data

(63) Continuation of application No. 13/450,420, filed on Apr. 18, 2012, now abandoned.

(60) Provisional application No. 61/476,726, filed on Apr. 18, 2011.

(51) Int. Cl.
*A61N 5/06* (2006.01)

(52) U.S. Cl.
CPC ............... *A61N 5/06* (2013.01); *A61N 5/0613* (2013.01); *A61N 2005/064* (2013.01); *A61N 2005/0632* (2013.01); *A61N 2005/0633* (2013.01); *A61N 2005/0654* (2013.01); *A61N 2005/0659* (2013.01); *A61N 2005/0667* (2013.01)

(58) Field of Classification Search
CPC ............ A61N 2005/0632; A61N 2005/0654; A61N 2005/0659; A61N 2005/0667; A61N 2005/0633; A61N 2005/064; A61N 5/06; A61N 5/0613
USPC ............................................. 606/90; 607/90
See application file for complete search history.

(56) References Cited

U.S. PATENT DOCUMENTS

| 1,183,949 | A | * | 5/1916 | Burdick | 607/90 |
|---|---|---|---|---|---|
| 2,954,771 | A | * | 10/1960 | Boyan | 607/90 |
| 3,062,987 | A | * | 11/1962 | Cuffman | 315/360 |
| 3,451,579 | A | * | 6/1969 | Bishop | 220/2.1 R |
| 4,202,326 | A | | 5/1980 | Van Gerpen | |
| 5,103,809 | A | | 4/1992 | DeLuca et al. | |
| 5,176,130 | A | | 1/1993 | Kim | |
| 5,441,531 | A | | 8/1995 | Zarate | |
| 5,716,331 | A | | 2/1998 | Chang | |
| 5,904,660 | A | | 5/1999 | Kim | |
| 5,976,097 | A | | 11/1999 | Jensen | |
| 6,024,760 | A | | 2/2000 | Marchesi | |
| 6,149,611 | A | | 11/2000 | Chen | |
| 6,200,282 | B1 | | 3/2001 | Furuie et al. | |
| 6,254,625 | B1 | | 7/2001 | Rosenthal | |
| 6,409,744 | B1 | * | 6/2002 | Marchesi | 607/96 |
| 6,682,495 | B2 | | 1/2004 | Park | |
| 7,198,634 | B2 | | 4/2007 | Harth et al. | |
| 7,341,310 | B1 | | 3/2008 | Ross | |
| 7,419,475 | B2 | | 9/2008 | Ferber et al. | |

(Continued)

FOREIGN PATENT DOCUMENTS

CN 201014318 Y * 1/2008
WO WO 2011100972 A1 * 8/2011

*Primary Examiner* — Gary Jackson
*Assistant Examiner* — Boniface N Nganga
(74) *Attorney, Agent, or Firm* — Carmela De Luca; Bereskin & Parr LLP

(57) ABSTRACT

An oscillating photo light therapy device includes a base and a light emitting unit pivotally mounted to the base. The light emitting unit is provided with at least one light emitting source. A movement imparting mechanism is provided for displacing the light emitting unit relative to the base along an oscillating motion, wherein the light source emits at different angles towards the user's body.

20 Claims, 6 Drawing Sheets

(56) References Cited

U.S. PATENT DOCUMENTS

| | | |
|---|---|---|
| 7,713,220 B2 | 5/2010 | Chen |
| 2004/0039428 A1 | 2/2004 | Williams et al. |
| 2005/0209538 A1 | 9/2005 | Lev et al. |
| 2006/0094993 A1 | 5/2006 | Hazard |
| 2007/0129711 A1* | 6/2007 | Altshuler ............ A45D 26/0061 606/9 |
| 2007/0293793 A1 | 12/2007 | Johnson |
| 2008/0208296 A1* | 8/2008 | Smith ............................. 607/89 |
| 2009/0005839 A1* | 1/2009 | Griffith ........................... 607/91 |
| 2009/0054217 A1 | 2/2009 | Teeter |
| 2009/0222070 A1 | 9/2009 | Daffer |
| 2010/0063487 A1 | 3/2010 | Van Straalen |
| 2011/0199770 A1* | 8/2011 | Pedersen ................... 362/249.03 |
| 2011/0224584 A1 | 9/2011 | Pryor et al. |
| 2012/0103963 A1 | 5/2012 | Milfeldt |
| 2012/0109041 A1 | 5/2012 | Munz |

\* cited by examiner

OSCILLATING PHOTO LIGHT THERAPY DEVICE

CROSS REFERENCE TO RELATED APPLICATIONS

This Application claims priority on U.S. Provisional Application No. 61/476,726, filed on Apr. 18, 2011, which is herein incorporated by reference.

FIELD OF THE INVENTION

The present invention relates to devices used in gyms and home gyms, for the well-being of users.

BACKGROUND OF THE INVENTION

In this age where people are concerned about their well-being and appearances, various methods, products and devices exist for exercising purposes, for improving one's skin texture, etc.

Nevertheless, there is a need in the art for improvements in the area of the well-being of people.

SUMMARY OF THE INVENTION

It is therefore an aim of the present invention to provide a novel device for the well-being of users thereof.

Therefore, in accordance with the present invention, there is provided an oscillating light therapy device, comprising a base and a light emitting unit, the light emitting unit being provided with at least one light source, a movement imparting mechanism being provided for displacing the light emitting unit relative to the base for providing an oscillating motion of the light emitting unit, wherein the light source emits towards the user's body.

Other objects, advantages and features of the present invention will become more apparent upon reading of the following non-restrictive description of embodiments thereof, given by way of example only with reference to the accompanying drawings.

BRIEF DESCRIPTION OF THE DRAWINGS

Reference will now be made to the accompanying drawings, showing by way of illustration an illustrative embodiment of the present invention, and in which.

DESCRIPTION OF ILLUSTRATIVE EMBODIMENTS OF THE INVENTION

With reference to the drawings, there will now be described an oscillating photo light therapy device D. The device D is herein shown in use as a user P is exercising on a treadmill T. The device D is to be used in gyms, home gyms, etc.

More particularly, the oscillating photo light therapy device D includes a ground-contacting base B and a light-emitting unit U mounted on the base B in such a way that the light-emitting unit U can oscillate with respect to the base B.

Figure 2:
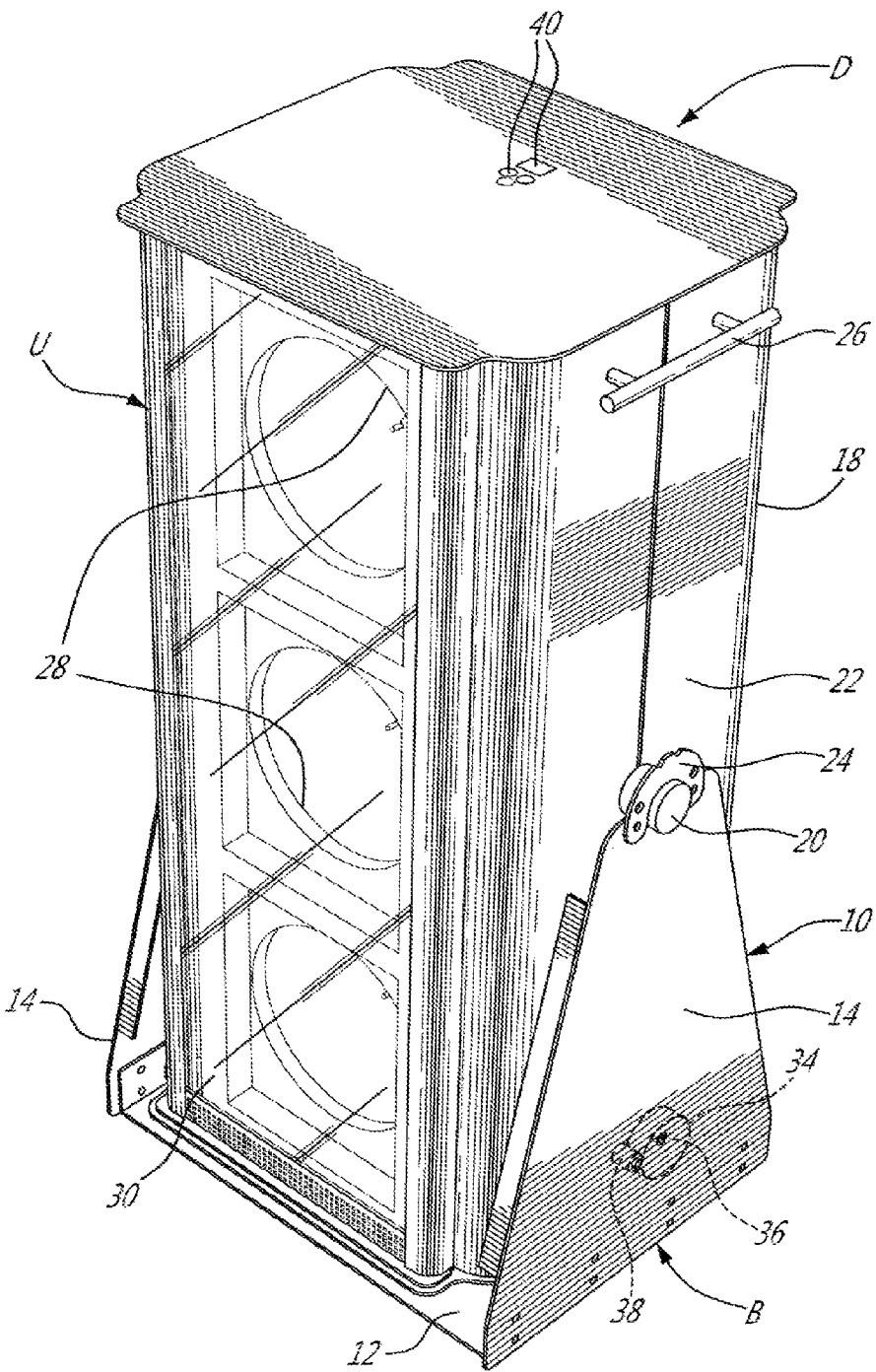
FIG. 2 is a perspective view of the oscillating photo light therapy device of FIG. 1.
Figure 3:
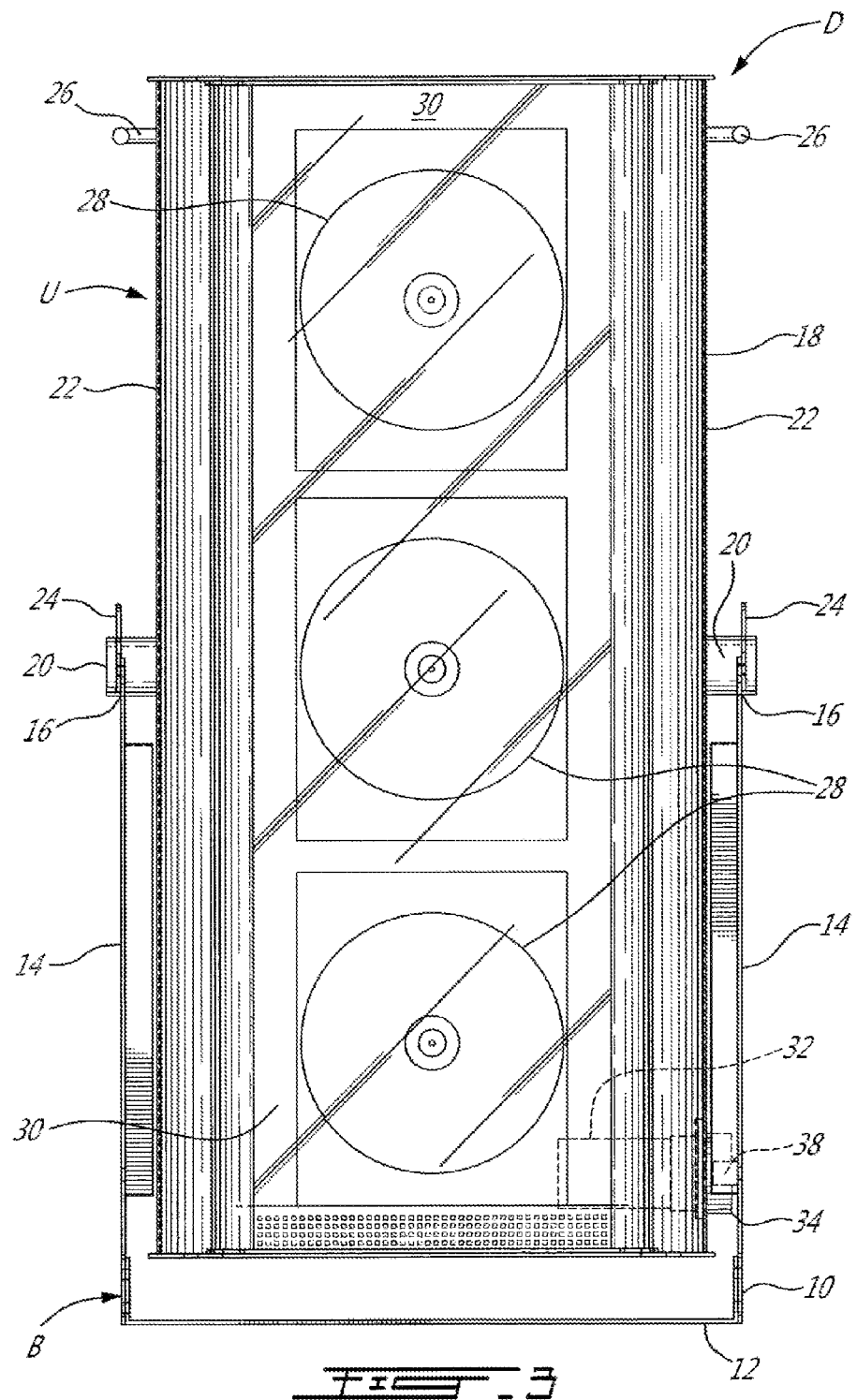
FIG. 3 is a front view of the oscillating photo light therapy device of FIG. 1.

As seen in FIGS. 2 and 3, the base B includes a U-shaped frame 10 having a lower support 12 adapted to overlie the ground and a pair of side support plates 14 extending vertically upwards from opposed lateral ends of the lower support 12. A substantially semi-circular recess 16 is defined in the upper end of each side support plate 14.

The light-emitting unit U includes a housing 18 extending between the side support plates 14. A pair of cylindrical members 20 are fixedly mounted to lateral walls 22 of the housing 18 so as to extend horizontally outwardly therefrom. Each cylindrical member 20 sits, by gravity, in a respective recess 16 of the side support plate 14 of the base B, thereby allowing the light-emitting unit U to pivot relative to the base B. Stopper plates 24 are mounted to the cylindrical members 20, outwardly of the side support plates 14 to ensure stability of the light-emitting unit U on the base B.

Handles 26 are mounted to the housing 18 for manipulating the light-emitting unit U.

Figure 1:
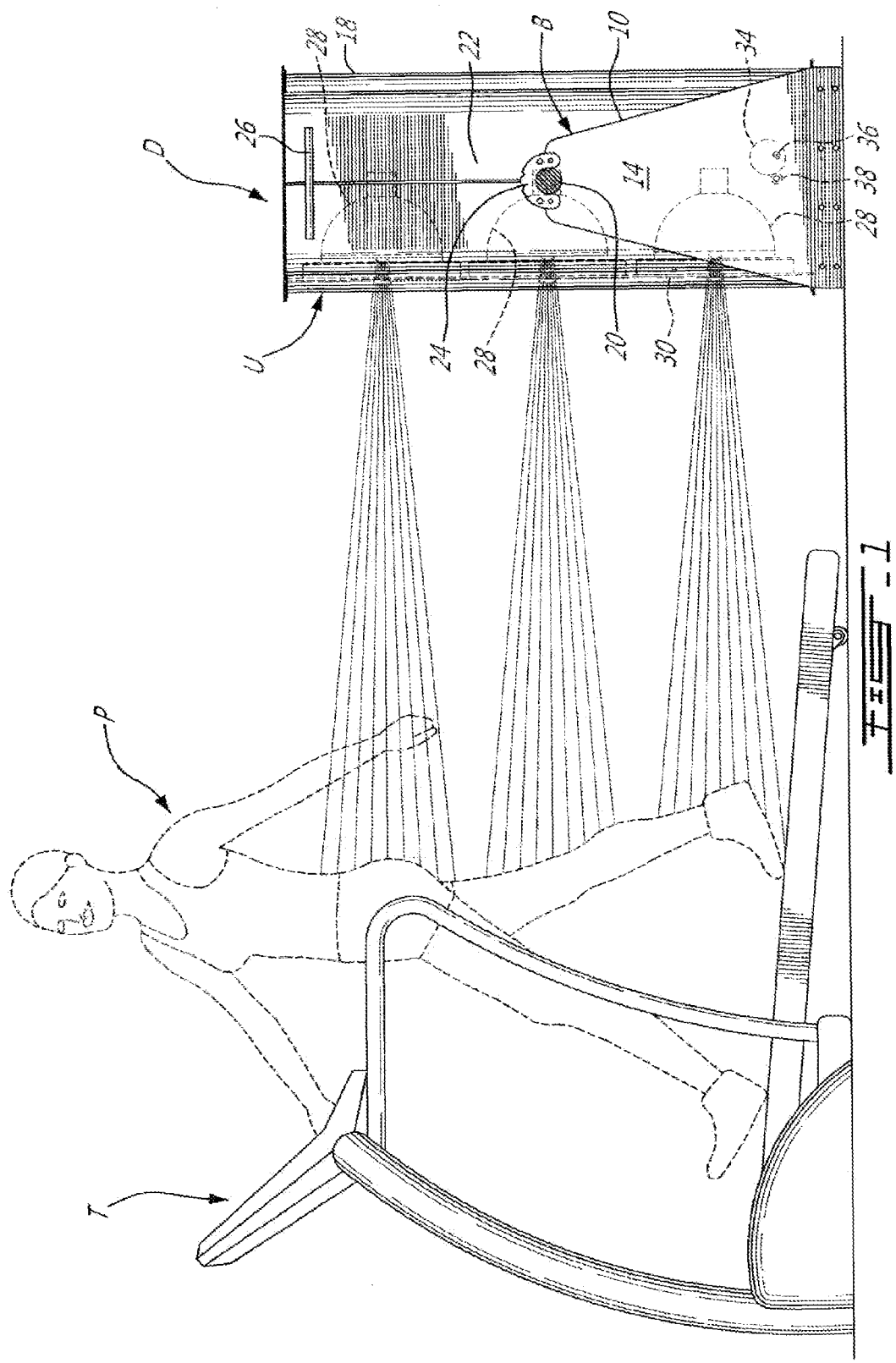
FIG. 1 is a side elevation view of an oscillating photo light therapy device in accordance with the present invention, and shown being used while a user is exercising on a treadmill.

A number (herein three) of infrared light emitting sources 28, such as specially formulated Quartz lamps, are mounted in the housing 18, as well seen in FIGS. 1 to 3. The three light emitting sources 28 are herein superposed, and a transparent protective sheet 30 (such as made of clear acrylic) is provided forwardly of the light emitting sources 28 as a shield that protects the users from touching any hot filter and components while allowing the transmission of the desired rays to the user U.

Figure 4:
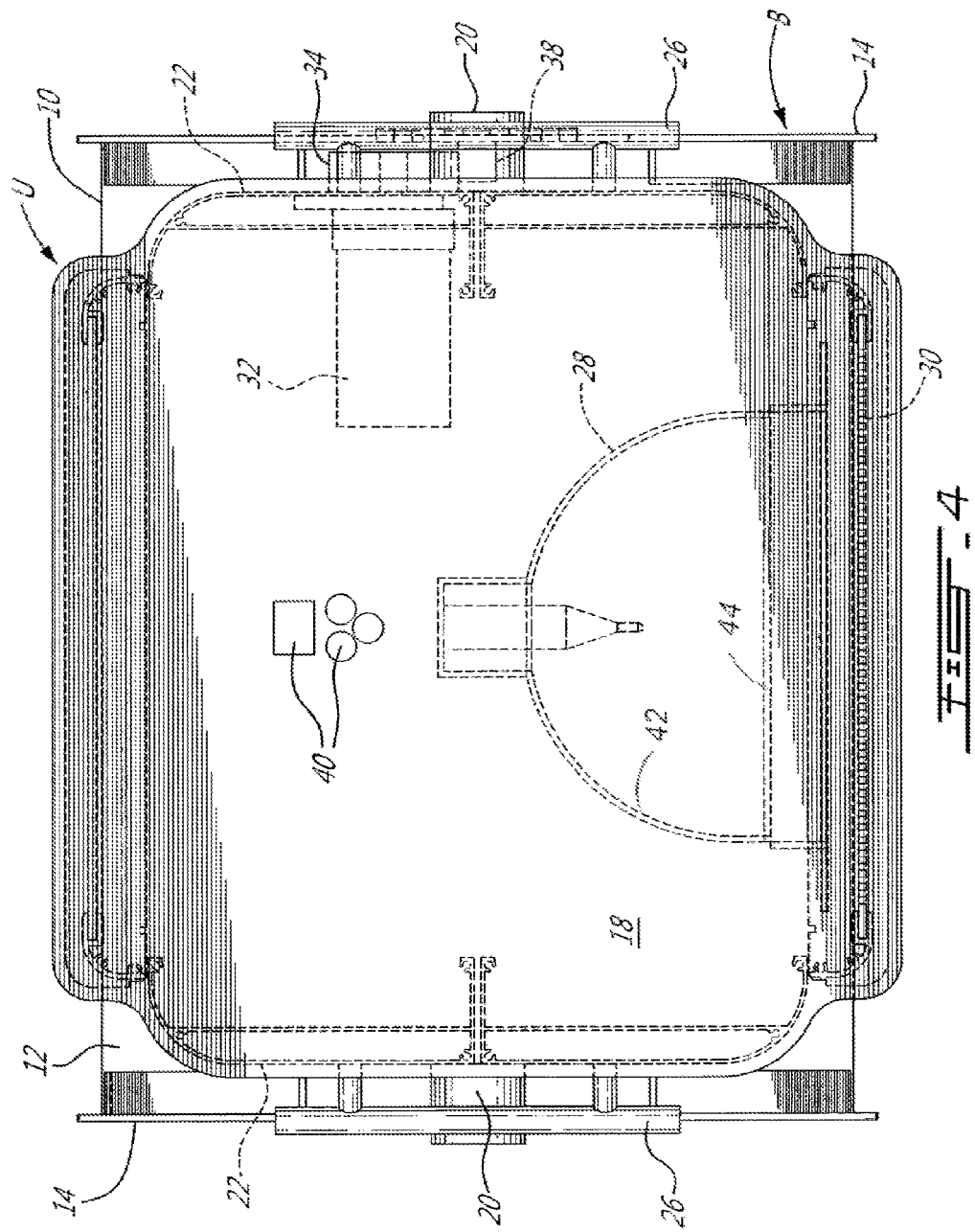
FIG. 4 is a top plan view of the oscillating photo light therapy device of FIG. 1.

Now referring mainly to FIGS. 3 and 4, a gear motor 32 is mounted in the housing 18 and a cylindrical drive member 34 is eccentrically mounted to an output shaft 36 of the gear motor 32. A roller 38 is mounted to one of the side support plates 14 of the base B, the roller 38 extending horizontally inwardly therefrom, that is towards the light-emitting unit U. The eccentric drive member 34 is adapted, for instance via gravity forces, into engagement with the roller 38.

Figure 5:
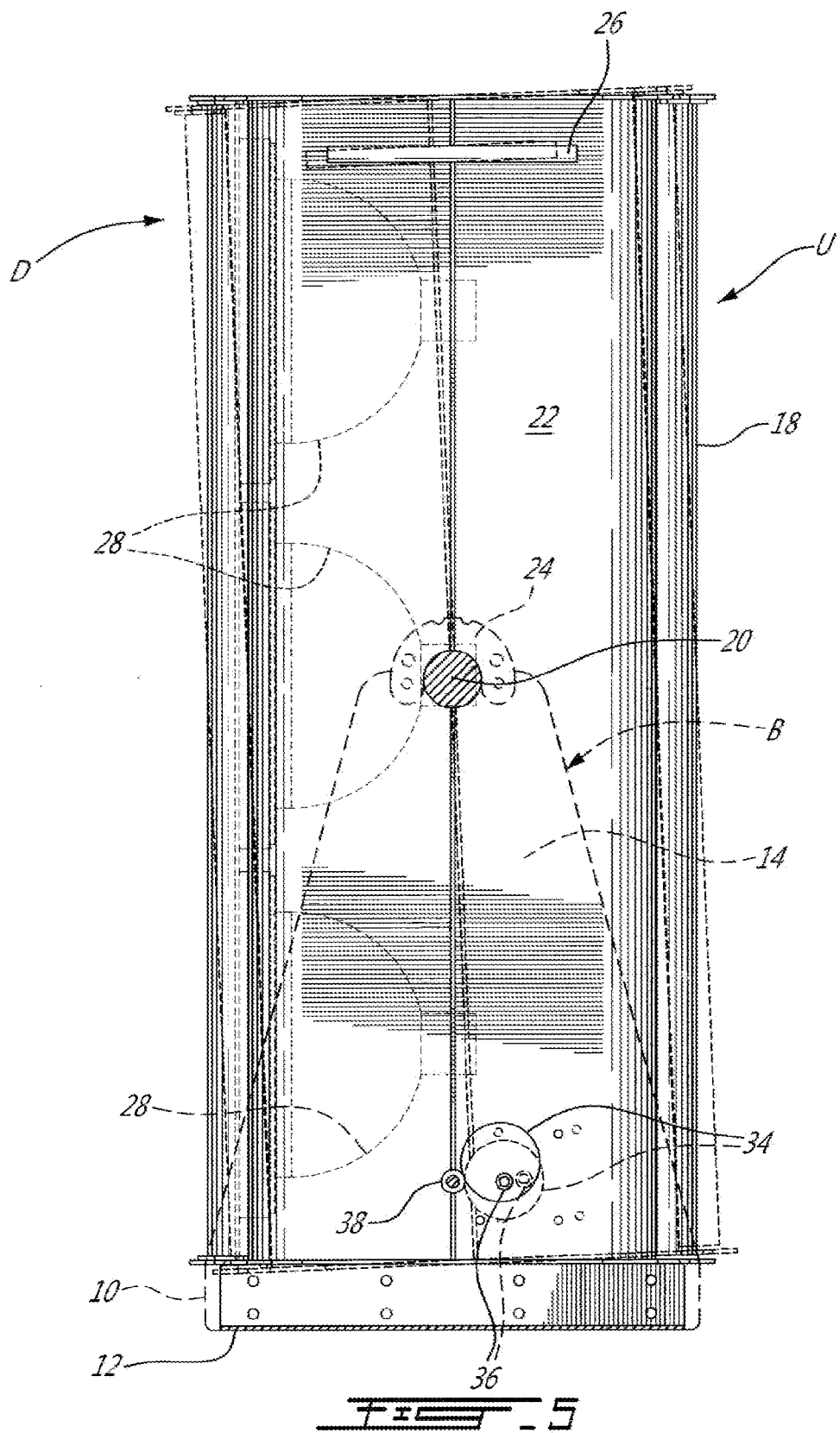
FIGS. 5 and 6 are right-side elevation views of the oscillating photo light therapy device of FIG. 1, showing the device in different positions.
Figure 6:
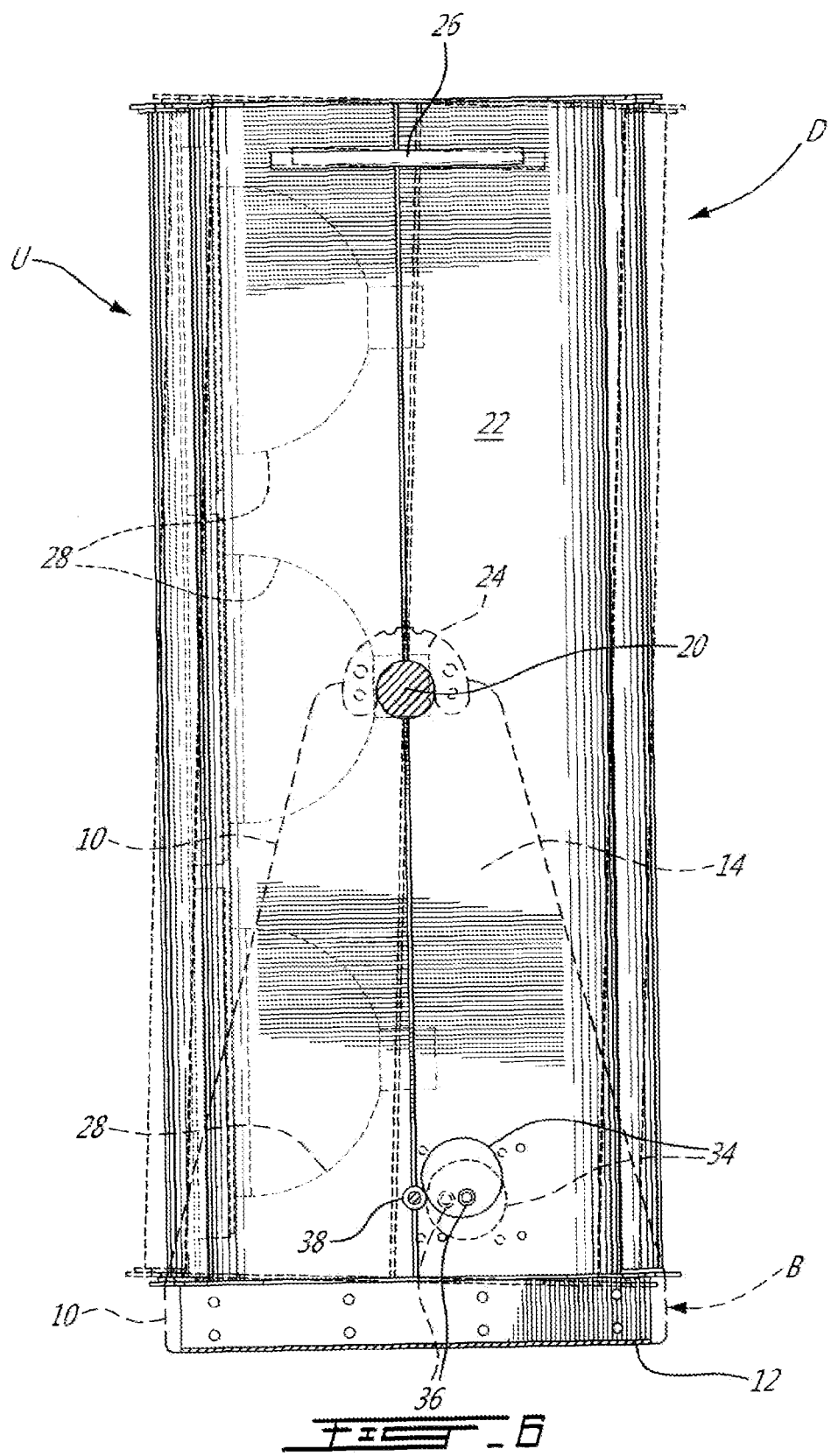

As the gear motor 32 and the eccentric drive member 34 turn, the roller 38, which is fixed to the base B, forces the light-emitting unit U to oscillate in view of the eccentricity of the drive member 34 relative to the output shaft 36 of the gear motor 32. FIG. 5 shows two positions (one in full lines and one in broken lines) of the drive member 34 as the two resulting positions (in corresponding full lines and broken lines) of the light-emitting unit U. FIG. 6 shows in broken lines a further position of the drive member 34 and the associated resulting position of the light-emitting unit U. Therefore, the continued rotation of the gear motor 32 causes the light-emitting unit U to oscillate. Other means to produce such oscillation can be contemplated. The movement of the light-emitting unit U and the actuation of the light emitting sources 28 is done via a control panel 40.

The light emitting sources 28 emit an ample amount of infrared energy from 633 to 900 nm range light spectrum (e.g. 633 nm, 700 nm or 852 nm), and are used along with parabolic reflectors 42 and selective narrow band transmitting glass filters 44 to produce an effective infrared photo light therapy on the thigh area of the user U while he/she utilizes the treadmill T. The light-emitting unit U oscillates for instance approximately 15 degrees every minute via the 1 RPM gear motor 32, thereby enabling the user U to receive uniform energy on his/her legs.

Device D can be used in a stand-alone vertical floor-mounted manner, behind the treadmill T of various manufacturers (as in FIG. 1) or it can be attached to the treadmill or other exercise machine by using clamps, bolts and other appropriate mechanical fastening devices.

This selected energy is able to reduce pore sizes, improve skin complexion, heal wounds faster, energize the lower epidermis for producing collagen and aid in gradually reducing cellulite.

The selective infrared energy is also able to penetrate approximately ½" in depth to increase the blood flow for even more benefits for training athletes.

The device D can be manufactured out of molded plastics or aluminum, metal extrusion and sheet metal formed panels. The ballasts that are enclosed power the light emitting sources 28 (e.g. quartz infrared lamps) while a fan cools the filters, the acrylic shield and other components.

A filter specifically made to eliminate the ultraviolet and some of the visible range wavelengths is provided for user's safety.

There is a safety switch that instantly turns the power off to the individual light emitting sources 28 in case that the filter is removed or cracked, broken, or shattered.

A totalizer type of hour counter records the hours of use to maintain the device D and replace lamps and other components. A digital timer that can have a maximum time exposure for the user's desire can start and stop the device D and can also be monitored remotely via a daisy chain system.

Although the present invention has been described hereinabove by way of embodiments thereof, it may be modified, without departing from the nature and teachings of the subject invention as described herein.

The invention claimed is:

1. An oscillating light therapy device comprising:
   a base having a pair of side support plates;
   a light emitting unit, the light emitting unit being provided with a housing, at least one light source, a parabolic reflector and a selective narrow band transmitting glass filter;
   a pair of cylindrical members mounted to the light emitting unit and extending horizontally outwardly from the housing, each of the pair of cylindrical members sitting, by gravity, in a recess of each of the side support plates, and providing a pivot point for a pivotal oscillating motion of the light emitting unit; and
   a movement imparting mechanism comprising a cylindrical drive member, a gear motor located inside the light emitting unit, and a roller mounted to the base and extending towards the light emitting unit, the cylindrical drive member being eccentrically mounted to an output shaft of the gear motor, the cylindrical drive member being adapted to engage, via gravity forces, with the roller;
   wherein the movement imparting mechanism is configured to pivotally displace the light emitting unit relative to the base along a 15° angle, providing the pivotal oscillating motion of the light emitting unit along a vertical plane; and
   wherein the at least one light source is configured to transmit light at wavelengths within a range of 633 nm to 900 nm and emits light forwardly of the base.

2. oscillating light therapy device as defined in claim 1, wherein the light emitting unit includes at least two light sources.

3. oscillating light therapy device as defined in claim 2, wherein the light sources are disposed one above the other.

4. oscillating light therapy device as defined in claim 1, wherein each light source is a quartz infrared lamp.

5. The oscillating light therapy device as defined in claim 1, wherein the movement imparting mechanism is configured to displace the light emitting unit along the 15° angle every minute.

6. oscillating light therapy device as defined in claim 1, wherein the filter is provided for eliminating unsafe ultraviolet and visible range wavelengths from the transmitted light.

7. The oscillating light therapy device of claim 1, wherein the pair of side support plates extending extends vertically upwardly from the base; and
   wherein the pair of cylindrical members supported by the side support plates to define the pivotal displacement of the light emitting unit relative to the base, and wherein the at least one light source mounted in the housing and oriented to emit light from a forward surface of the housing.

8. An oscillating light therapy device in combination with an exercise machine, the exercise machine being adapted to be used by a user, the light therapy device comprising:
   a base having a pair of side support plates;
   a light emitting unit, the light emitting unit being provided with a housing, at least one light source, a parabolic reflector and a selective narrow band transmitting glass filter;
   a pair of cylindrical members mounted to the light emitting unit and extending horizontally outwardly from the housing, each of the pair of cylindrical members sitting, by gravity, in a recess of each of the side support plates, and providing a pivot point for a pivotal oscillating motion of the light emitting unit; and
   a movement imparting mechanism comprising a cylindrical drive member, a gear motor located inside the light emitting unit, and a roller mounted to the base and extending towards the light emitting unit, the cylindrical drive member being eccentrically mounted to an output shaft of the gear motor, the cylindrical drive member being adapted to engage, via gravity forces, with the roller; wherein the movement imparting mechanism is configured to pivotally displace the light emitting unit relative to the base along a 15° angle, providing the pivotal oscillating motion of the light emitting unit along a vertical plane; and
   wherein the at least one light source is configured to transmit light at wavelengths within a range of 633 nm to 900 nm and emits light forwardly of the base.

9. The combination of claim 8, wherein the light emitting unit includes at least two light sources.

10. The combination of claim 9, wherein the light sources are disposed one above the other.

11. The combination of claim 8, wherein each light source is a quartz infrared lamp.

12. The combination of claim 8, wherein the movement imparting mechanism is configured to displace the light emitting unit along the 15° angle every minute.

13. The combination of claim 8, wherein the filter is provided for eliminating unsafe ultraviolet and visible range wavelengths from the transmitted light.

14. The combination of claim 8, wherein the exercise machine is a treadmill on which the user is standing, with the light emitting unit being positioned behind the user and with the light emitting unit being directed towards the user.

15. The combination of claim 8, wherein the pair of side support plates extending extends vertically upwardly from the base; and
   wherein the pair of cylindrical members supported by the side support plates to define the pivotal displacement of the light emitting unit relative to the base, and wherein the at least one light source mounted in the housing and oriented to emit light from a forward surface of the housing.

16. An oscillating light therapy device comprising:
a base having a pair of side support plates;
a light emitting unit, the light emitting unit being provided with at least one light source, a parabolic reflector and a selective narrow band transmitting glass filter;
a pair of cylindrical members mounted to the light emitting unit and extending horizontally outwardly therefrom, each of the pair of cylindrical members sitting, by gravity, in a recess of each of the side support plates, and providing a pivot point for a pivotal oscillating motion of the light emitting unit; and
a movement imparting mechanism comprising a cylindrical drive member, a gear motor located inside the light emitting unit, and a roller mounted to the base and extending towards the light emitting unit, the cylindrical drive member being eccentrically mounted to an output shaft of the gear motor, the cylindrical drive member being adapted to engage, via gravity forces, with the roller;

wherein the movement imparting mechanism is configured to pivotally displace the light emitting unit relative to the base, providing the pivotal oscillating motion of the light emitting unit along a vertical plane; and wherein the at least one light source is configured to transmit light at wavelengths within a range of 633 nm to 900 nm and emits light forwardly of the base.

17. An oscillating light therapy device as defined in claim 16, wherein the light emitting unit includes at least two light sources.

18. An oscillating light therapy device as defined in claim 16, wherein the light sources are disposed one above the other.

19. An oscillating light therapy device as defined in claim 16, wherein each light source is a quartz infrared lamp.

20. The combination of claim 8, wherein the movement imparting mechanism is configured to displace the light emitting unit along the 15° angle every minute.

* * * * *